United States Patent
Fossel

(10) Patent No.: US 7,629,384 B2
(45) Date of Patent: *Dec. 8, 2009

(54) TOPICAL DELIVERY OF L-ARGININE TO CAUSE BENEFICIAL EFFECTS

(75) Inventor: Eric T. Fossel, Newton, MA (US)

(73) Assignee: Strategic Science & Technologies, LLC, Cambridge, MA (US)

( * ) Notice: Subject to any disclaimer, the term of this patent is extended or adjusted under 35 U.S.C. 154(b) by 520 days.

This patent is subject to a terminal disclaimer.

(21) Appl. No.: 10/201,635

(22) Filed: Jul. 22, 2002

(65) Prior Publication Data

US 2003/0028169 A1    Feb. 6, 2003

Related U.S. Application Data

(63) Continuation-in-part of application No. 08/932,227, filed on Sep. 17, 1997.

(51) Int. Cl.
*A61K 31/195* (2006.01)
*A61K 31/198* (2006.01)
*A61K 9/127* (2006.01)
*A61P 15/10* (2006.01)
*A61P 17/14* (2006.01)
*A61P 9/08* (2006.01)

(52) U.S. Cl. ............... 514/565; 424/450; 514/801; 514/880; 514/929; 514/946

(58) Field of Classification Search .......... 514/565
See application file for complete search history.

(56) References Cited

U.S. PATENT DOCUMENTS

| | | |
|---|---|---|
| 4,681,897 A | 7/1987 | Brand |
| 4,702,903 A | 10/1987 | Keefer |
| 4,732,892 A | 3/1988 | Sarpotdar et al. |
| 4,871,839 A | 10/1989 | Gibson |
| 4,950,654 A | 8/1990 | Horn et al. |
| 4,976,952 A | 12/1990 | Lang et al. |
| 5,028,435 A | 7/1991 | Katz et al. |
| 5,180,743 A | 1/1993 | Watanabe et al. |
| 5,254,331 A | 10/1993 | Mausner |
| 5,332,758 A | 7/1994 | Nakata et al. |
| 5,391,550 A | 2/1995 | Carniglia et al. |
| 5,405,919 A | 4/1995 | Keefer et al. |
| 5,428,070 A | 6/1995 | Cooke et al. |
| 5,439,938 A * | 8/1995 | Snyder et al. ............. 514/565 |
| 5,476,852 A | 12/1995 | Cauwenbergh |
| 5,505,958 A | 4/1996 | Bello et al. |
| 5,538,740 A | 7/1996 | Abad |
| 5,543,430 A | 8/1996 | Kaesemeyer |
| 5,576,351 A | 11/1996 | Yoshimura et al. |
| 5,595,753 A | 1/1997 | Hechtman |
| 5,629,002 A | 5/1997 | Weuffen et al. |
| 5,632,981 A | 5/1997 | Saavedra et al. |
| 5,648,101 A | 7/1997 | Tawashi |
| 5,691,423 A | 11/1997 | Smith et al. |
| 5,698,738 A | 12/1997 | Garfield et al. |
| 5,714,472 A | 2/1998 | Gray et al. |
| 5,762,963 A | 6/1998 | Byas-Smith |
| 5,789,442 A | 8/1998 | Garfield et al. |
| 5,853,768 A | 12/1998 | Altadonna |
| 5,891,459 A | 4/1999 | Cooke et al. |
| 5,895,658 A | 4/1999 | Fossel |
| 5,922,332 A | 7/1999 | Fossel |
| 5,925,372 A | 7/1999 | Berner et al. |
| 5,939,094 A | 8/1999 | Durif et al. |
| 6,036,977 A | 3/2000 | Drizen et al. |
| 6,103,275 A | 8/2000 | Seitz et al. |
| 6,117,872 A | 9/2000 | Maxwell et al. |
| 6,207,713 B1 * | 3/2001 | Fossel ............. 514/565 |
| 6,242,229 B1 | 6/2001 | Pineau |
| 6,375,672 B1 | 4/2002 | Aksan et al. |
| 6,387,081 B1 | 5/2002 | Cooper |
| 6,448,267 B1 | 9/2002 | Anggard et al. |
| 6,451,337 B1 | 9/2002 | Smith et al. |
| 6,458,841 B2 * | 10/2002 | Fossel ............. 514/565 |
| 6,511,991 B2 | 1/2003 | Hrabie et al. |
| 6,538,033 B2 | 3/2003 | Bing |

(Continued)

FOREIGN PATENT DOCUMENTS

DE    10128910 A1    12/2002

(Continued)

OTHER PUBLICATIONS

The Merck Index (12th Ed. 1996), p. 132.*

(Continued)

*Primary Examiner*—John Pak
(74) *Attorney, Agent, or Firm*—Wolf, Greenfield & Sacks, P.C.

(57) ABSTRACT

The application of L-arginine and its derivatives to the skin causes beneficial effects of wound healing, increasing erectile function and increased growth of hair when applied in sufficient quantity to the skin. A hostile biophysical agent may be combined with the L-arginine to increase its absorption into the skin. The desired concentrations of the hostile biophysical agent is increased when concentration of L-arginine is less than 20% of the concentration of the substance applied to maximize its effect.

4 Claims, No Drawings

U.S. PATENT DOCUMENTS

| | | | |
|---|---|---|---|
| 6,617,337 | B1 | 9/2003 | Wilcox |
| 6,716,436 | B1 | 4/2004 | Seguin |
| 6,747,063 | B2 * | 6/2004 | Adams et al. ............... 514/573 |
| 2002/0015713 | A1 | 2/2002 | Murdock et al. |
| 2002/0037854 | A1 | 3/2002 | Breton et al. |
| 2002/0168325 | A1 | 11/2002 | Lerner et al. |
| 2002/0168424 | A1 | 11/2002 | Shahinpoor et al. |

FOREIGN PATENT DOCUMENTS

| | | |
|---|---|---|
| EP | 0338291 A1 | 10/1989 |
| EP | 0391342 A1 | 10/1990 |
| EP | 1210933 A1 | 6/2002 |
| FR | 1553063 | 11/1967 |
| FR | 5940 | 4/1968 |
| FR | 2602678 | 2/1988 |
| FR | 2740453 A1 * | 4/1997 |
| FR | 2810540 A1 | 12/2001 |
| GB | 2094142 A1 | 9/1982 |
| JP | 04-005231 | 9/1992 |
| JP | 6-247832 | 9/1994 |
| JP | 7-53336 | 2/1995 |
| JP | 09241156 A * | 9/1997 |
| WO | WO 88/06034 A1 | 8/1988 |
| WO | WO 92/08705 | 5/1992 |
| WO | WO 9409750 A1 * | 5/1994 |
| WO | WO 95/13060 | 5/1995 |
| WO | 95/15147 | 6/1995 |
| WO | WO 95/15147 | 6/1995 |
| WO | WO 96/08966 A1 | 9/1995 |
| WO | WO 96/14748 | 5/1996 |
| WO | WO 96/29988 A1 | 10/1996 |
| WO | WO 97/16983 | 5/1997 |
| WO | WO 9739760 A1 * | 10/1997 |
| WO | WO 99/13717 A1 | 3/1999 |
| WO | WO 00/03689 A2 | 1/2000 |
| WO | WO 00/40215 A1 | 7/2000 |
| WO | WO 00/54773 A1 | 9/2000 |
| WO | WO 00/69469 A1 | 11/2000 |
| WO | WO 01/45713 A1 | 6/2001 |

OTHER PUBLICATIONS

Hirvonen et al., Effect of diffusion potential, osmosis and ion-exchange on transdermal drug delivery: theory and experiments, Journal of Controlled Release (1998), vol. 56, pp. 33-39.*

International Search Report for International Application Serial No. PCT/US05/05726 dated Sep. 9, 2005.

International Search Report for International Application Serial No. PCT/US05/13228 dated Jul. 5, 2005.

International Search Report for International Application Serial No. PCT/US05/13230 dated Oct. 28, 2005.

International Search Report for International Application Serial No. PCT/US98/19429, international filing date Sep. 17, 1998.

Cooper, Eugene R., et al., "Penetration Enhancers" in: Transdermal Delivery of Drugs, Kydonieus and Berner (ed), CRC Press, Boca Raton, 1987, p. 57-62.

Riedel, Markus W., et al., "Different Mechanisms of L-arginine Induced Dilation of Brain Arterioles in Normotensive and Hypertensive Rats", CA: 122 (11) 130053t (Abstract).

Argiolas, A., et al., "Nitric Oxide is a Central Mediator of Penile Erection," Neuropharmacology, vol. 11, pp. 1339-1344 (1994).

Birder et al., "Adrenergic- and capsaicin-evoked nitric oxide release from urothelium and afferent nerves in urinary bladder," Chemical Abstracts (1998:548084), vol. 129, No. 255375.

Bunker, C.D., "Alteration in scalp blood flow after the epicutaneous application of 3% minoxidil and 0.1% hexyl nicotinate in alopecia," Correspondence, pp. 669.

DeBoer, E.M., "Does Topical Minoxidil Increase Skin Blood Flow? A Laser Doppler Flowmetry Study," Acta Derm Venereo, vol. 68, pp. 271-274 (1988).

Dietz, N. M., "Is nitric oxide involved in cutaneous vasodilation during body heating in humans?", J. Appl. Physiol., vol. 76, No. 5, pp. 2047-2053 (1994).

Garban, H., "Effect of aging on nitric oxide-mediated penile erection in rats," Am. J. Physiol., vol. 268, pp. 467-475 (1995).

I-Sheng, T., "Evaluation of Vasulogenic Impotence Using Dynamic Penile Washout Test," J. Formosan Med. Assoc., vol. 89, No. 11, pp. 992-996 (1990).

Kirkeby, H.J., "Role of the L-arginine/nitric oxide pathway in relaxation of isolated human penile cavernous tissue and circumflex veins," Acta Physiol Scand, vol. 149, pp. 385-392 (1993).

Klemp, P., "Subcutaneous Blood Flow in Early Male Patter Baldness," J. Invest Dermatol, vol. 92, pp. 725-726 (1989).

Laan, E., et al., "Assessment of female sexual arousal: Response specificity and construct validity," Psychophysiology, vol. 32, pp. 476-485 (1995).

Mathias, B. J. et al., "Topical Capsaicin for Chronic Neck Pain," Am. J. Phys. Med. Rehabil., vol. 74, No. 1, pp. 39-44 (1995).

Moody, J.A., et al., "Effects of Long-Term Oral Administration of L-Arginine of the Rat Erectile Response," American Urological Association, Inc., vol. 158, pp. 942-947 (1997).

Owen, J.A., et al., "Topical Nitroglycerin: A Potential Treatment for Impotence," The Journal of Urology, vol. 141, pp. 546-548 (1989).

Pauly et al, Liposomes containing amino acids and peptides and proteins for skin care, Chemical Abstracts (1998), vol. 113, No. 65069.

Singh, S. et al., "Response to digital arteries to endothelium dependent and independent vasocilators in patients with Raynaud's phenomenon," European Journal of Clinical Investigation, vol. 25, pp. 182-185 (1995).

Sonntag, M., et al., "Role of nitric oxide in local blood flow control in the anaesthetized dog," European Journal of Physiology, pp. 194-199 (1992).

Tseng, L.F., et al., "Increase of nitric oxide production by L-arginine potentiates i.c.v. administered β-endorphin-induced antinociception in the mouse," European Jouranal of Pharmacology, vol. 212, pp. 301-303 (1992).

Wang, R. et al., "Nitric Oxide Mediates Penile Erection in Cats," The Journal of Urology, vol. 151, pp. 234-237 (1994).

Whitmore, S.E., et al, "Acute Effect of Topical Minoxidil on Digital Blood Flow in Patients with Raynaud's Phenomenon," The Journal of Rheumatology, vol. 11, No. 1, pp. 50-54 (1995).

Riedel, Markus W., et al., "Different Mechanisms of L-arginine Induced Dilation of Brain Arterioles in Normotensive and Hypertensive Rats", CA: 122(11) 130053t (Abstract), (1995).

Bunker, C.D., "Alteration in scalp blood flow after the epicutaneous application of 3% minoxidil and 0.1% hexyl nicotinate in alopecia," Correspondence, pp. 669, (1986).

Fossel, Eric T. "Improvement of Temperature and Flow in Feet of Subjects with Diabetes With Use of a Transdermal Preparation of L-Arginine" Diabetes Care, vol. 27, No. 1, Jan. 2004, pp. 284-285.

Haldiya, Kripa Ram et al. "Dermal Ulcers and Hypertension in Salt Workers" Current Science, vol. 87, No. 8, Oct. 25, 2004, pp. 1139-1141.

Matuszak, Daniel et al. "Thermodynamic Driving Force for Molecular Diffusion—Lattice Density Functional Theory Predictions" J. Non-Equilib. Thermodyn. 2006 vol. 31, pp. 355-384.

Schölermann, A. et al. "Clinical and biophysical efficacy of a novel coenzyme $Q_{10}$ containing anit-wrinkle cream (Eucerin® Q10 active)" J EP Acad Dermatol Venereol, 11:S270, year unknown.

Suhonen, T. Marjukka et al. "Epidermal Cell Culture Model Derived From Rat Keratinocytes with Permeability Characteristics Comparable To Human Cadaver Skin" European Journal of Pharmaceutical Sciences 20 (2003) pp. 107-113.

Nakaki, T. et al., "Beneficial Circulatory Effect of $_L$-Arginine," Jpn. J. Pharmacol. 66, 167-171 (1994).

* cited by examiner

TOPICAL DELIVERY OF L-ARGININE TO CAUSE BENEFICIAL EFFECTS

This is a continuation in part of application Ser. No. 08/932,227 filed Sep. 17, 1997, the contents of which are incorporated by their entirety.

BACKGROUND

1. Field of the Invention

This invention relates to topical application of a cream, gel, or other vehicle which contains substances such as L-arginine which delivers these substances into tissue for the purpose of producing beneficial effects such as growth of hair on the scalp, healing of leg ulcers secondary to diabetes or confinement to bed and overcoming erectile dysfunction, as well as beneficial effects through restoration of natural mechanisms based on improvement of local blood supply.

2. Prior Art

Approaches to improving local blood flow have been many and consist of both systemic and topical approaches. Many beneficial effects could be obtained should improvement in local blood flow be achieved since impairment of local blood flow causes a variety of negative consequences.

It has been recognized that deficiencies in blood flow in the scalp occur in male pattern baldness. See G. Duplecnain et al., *J. Louisiana State Med Soc.* 146, 7 (1994); P Klemp et al., *J Invests Dermatol* 95, 725 (1989); S Toshitani et al., *J Dermatol* 17, 240 (1990). Topical minoxidil has been used as an agent for hair growth in male pattern baldness with varying results. Though the suggestion has been made that minoxidil operates through increase in the blood supply to the scalp, many investigators have failed to show such an effect. See E de Boer et al., *Acta Dermato-Venereoligica* 68, 271 (1988); C Bunker et al., *British J Derm* 117, 668 (1987).

It has long been recognized that impaired blood flow to the penis is a major cause of erectile failure (impotence) in men. See A Moradian et al. *Am J. Med* 85, 748, (1988); T Hwang et al. *J Formosan Med Assoc* 89, 992 (1990). Further it has been recognized by using isolated tissue in vitro and in animal experiments that nitric oxide is an important mediator of relaxation of the vessels in penile cavernous tissue. See H Kirkeby et al. *Acta Physiol Scand* 149, 385 (1993). Topical nitroglycerine has been used in the treatment of impotence because of its ability to dilate vessels. The results were inconclusive and the treatment not well tolerated because of the cardiac response to nitroglycerine. See S Negelev *J Urology* 143, 586 (1990).

Accordingly, several objects and advantages of the instant invention are to induce the growth of hair on portions of human scalp which has insufficient hairby means of enhancement of the body's natural mechanisms. It is yet another object of the instant invention to induce healing of superficial ulcers of the limbs by means of enhancement of the body's natural mechanisms. It is still another object of the instant invention to overcome erectile failure restoring natural male sexual function by means of enhancement of the body's own natural mechanisms.

SUMMARY OF THE INVENTION

It was discovered that topical application of a nitric oxide precursor, L-arginine, in its various forms contained in a variety of topical preparations, either by themselves or with other agents to aid in penetration, such as a high ionic strength environment, neutralization of its charge in a complex or by other means, or included in a liposome or other biological carrier, when administered to the scalp causes hair growth, when administered to superficial ulcers causes healing and when administered to the penis enhances erectile function. Increasing the levels of concentration of penetrants in combination with reduced amounts of L-arginine maintains effective treatment concentrations.

In one embodiment of the invention, a penetrating cream containing L-arginine at an effective concentration and a salt, such as sodium chloride, at a concentration sufficient to create a hostile biophysical environment for the L-arginine in the cream is applied to nightly to the scalp containing a deficit of hair induces hair growth within 3-4 months.

Further, in accordance with this invention, a penetrating cream containing L-arginine in a concentration sufficient to produce the desired effect along with sodium chloride or other salts at a concentration sufficient to produce a hostile biophysical environment when applied to the penis induces firm and natural erections within 20 minutes.

Consequently, with the discovery of the present invention, a means to restore hair growth on a portion of scalp scarce in hair has been found. Further, with the discovery of the present invention, a means to heal superficial ulcers has been found. Additionally, with the discovery of the present invention, a means to overcome erectile dysfunction has been found.

In preferred embodiments, the delivery vehicle is a penetrating cream, the L-arginine is present as L-arginine hydrochloride in a concentration sufficient to produce the desired effect and the agent which creates the hostile biophysical environment is sodium chloride at a concentration sufficient to aid in tissue absorption. L-arginine or its derivatives are present in a concentration of 1% to 35%, with preferred concentrations 5% to 35%, and 12% to 35% better. These and other objects and features of the present invention will become apparent to those skilled in the art from reading the description of the invention, which follows.

DETAILED DESCRIPTION OF THE INVENTION

The preferred embodiment consists of a base cream with the properties of excellent absorption into the skin which also contains L-arginine hydrochloride (12.5% w/v), choline chloride (10%), sodium chloride (5% w/v) and magnesium chloride (5% w/v). The components of the base cream may be those commonly found in hand creams, such as water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A & D, triethanolamine, methylparaben, aloe vera extract, imidazolidinyl urea, propylparaben, and BHA. L-arginine hydrochloride provides a precursor to the molecule, nitric oxide, NO. Nitric oxide is the substance that relaxes the blood vessels, allowing for increased blood flow. Choline chloride, sodium chloride and magnesium chloride provides a high ionic strength environment for the highly charged molecule, L-arginine. This high ionic strength environment is an example of a hostile biophysical environment for L-arginine. That is, the highly charged ionic strength is an unfavorable environment for the highly charged L-arginine making the L-arginine anxious to move to a more hospitable, less charged environment such as human tissue. The base cream containing L-arginine, choline chloride, sodium chloride and magnesium chloride is the agent which produces beneficial effects such as hair growth, healing of ulcers such as leg ulcers or restoration of normal erectile function in males suffering from erectile dysfunction.

The cream acts effectively to induce hair growth on human scalp lacking sufficient hair when applied nightly to the bald area each night for several months. Hair growth is naturally a slow process. However, substantial hair growth is achieved over large areas of scalp with results becoming evident in a few weeks and substantial within several months. Yet further, the cream acts to promote healing of superficial ulcers such as those sometimes found on the legs of persons with severe diabetes. Application twice daily for a period of two weeks causes substantial healing and in many cases complete healing is achieved within this time period or slightly longer (3-4 weeks). Still further, the cream acts to overcome erectile dysfunction in males causing restoration of natural sexual function. These applications and others share as a common mechanism of action, improvement in local blood flow.

OTHER EMBODIMENTS

In one embodiment, the topical delivery vehicle of the present invention comprises:

L-arginine hydrochloride at a concentration of 0.25% to 25% by weight, wherein the L-arginine hydrochloride is contained in a package selected from the group consisting of liposomes, emulsions of collagen, collagen peptides and combinations thereof, wherein the delivery vehicle further comprises an ion donor selected from the group consisting of sodium chloride, choline chloride, potassium chloride, lithium chloride and magnesium chloride and mixtures thereof, and said ion donor is present in an amount sufficient to create a high ionic strength environment able to cause the L-arginine hydrochloride to migrate from the delivery vehicle to the skin where the delivery vehicle is applied, wherein (i) said ion donor concentration in the delivery vehicle is 10% to 90% by weight when the concentration of L-arginine hydrochloride in the delivery vehicle is 0.25% to below 5% by weight, (ii) said ion donor concentration in the delivery vehicle is 5% to 80% by weight when the concentration of L-arginine hydrochloride in the delivery vehicle is 5% to 15% by weight, and (iii) said ion donor concentration in the delivery vehicle is 5% to 50% by weight when the concentration of L-arginine hydrochloride in the delivery vehicle is greater than 15% to 25% by weight.

Other Active Agents

While L-arginine hydrochloride is the preferred active agent because it is the agent in nature itself, it is non-toxic, is highly soluble and it is inexpensive, other agents could be used which are also precursors or donors of nitric oxide. These include D,L -arginine, L-arginine, alkyl (ethyl, methyl, propyl, isopropyl, butyl, isobutyl, t-butyl) esters of L-arginine and salts thereof. Pharmaceutically acceptable salts include hydrochloride, glutamate, butyrate, and glycolate. L-arginine concentrations desired are 1% to 35%, with 5% to 35% more effective with 12% to 35% best.

In the case of an alternative active agent were used it would be simply substituted for L-arginine in a delivery preparation and the preparation used as in the case of the L-arginine preparation.

Other Means of Effecting or Improving Absorption

A variety of means for effecting or improving absorption of the active agent can be envisioned. One principle behind the absorption of a highly charged molecule such as L-arginine into tissue is to either create a biophysically hostile environment in the delivery vehicle such that L-arginine would prefer to be in tissue, or to package L-arginine in such a way that it is carried into tissue or neutralize its charge by derivitization or forming a neutral salt. Examples of biophysically hostile environments, include but are not limited to; high ionic strength by the addition of ionic salts such as sodium chloride, magnesium chloride or choline chloride; high or low pH by adding pharmaceutically acceptable acids or bases; and highly hydrophobic environments by decreasing water content and increasing lipid, oil and/or wax content. Examples of packaging which would be carried into tissue includes liposomes or emulsions of collagen, collagen peptides or other components of skin or basement membrane. Examples of neutralization of charge include delivery of the active agent in the form or an ester or salt such as arginine glutamate which is electronically neutral.

In each case of creating a hostile biophysical environment for the active agent, the agent was added to an appropriate preparation. In the case of creating a high ionic strength ions such as but not limited to sodium chloride, potassium chloride, choline chloride, magnesium chloride, lithium chloride, alone or in combination were added in high concentration. Other highly charged molecules such as polylysine, polyglutamine, polyaspartate or copolymers of such charged amino acids may be used to create the hostile biophysical environment. Alternatively a hostile biophysical environment may be created by placing the highly charged L-arginine in an hydrophobic, oily environment such as in an oil-based cream containing little or no water. Absorption may further be aided by combining the use of hostile biophysical environments with the use of penetrating agents such as oleoresin capsicum or its constituents or molecules containing heterocyclic rings to which are attached hydrocarbon chains.

EXAMPLE 1

In this example a 53 year old man with a scalp lacking sufficient hair consisting of a severely receding hairline as well as large "bald spot" on the top rear of his head was provided with a penetrating cream containing L-arginine hydrochloride (12.5% w/v), choline chloride (10% w/v), sodium chloride (5% w/v) and magnesium chloride (5% w/v). The cream was applied to the bald areas each night before going to bed and was rubbed in extensively for maximal absorption. New hair growth was noted within 2-3 weeks. Within 4 months the receding hairline (previously 4 cm of bald skin) had returned to normal and the "bald spot" previously more than 7 cm in diameter had been reduced to an area of less than 2 cm with even this area showing some new hair growth.

EXAMPLE 2

In a 54 year old man with a history of impotence twice daily administration of a penetrating cream containing L-arginine hydrochloride (12.5% w/v), choline chloride (10% w/v), sodium chloride (10% w/v) and magnesium chloride (5% w/v) directly to the penis twice daily for 7 days brought initial relief from the symptoms of impotence and allowed the subject to resume normal sexual activity. This relief of symptoms was maintained by continuation of the treatment daily.

EXAMPLE 3

In a 62 year old man with a history of impotence placed a condom containing a water based penetrating cream containing L-arginine hydrochloride (12.5% w/v), choline chloride (10% w/v), sodium chloride (5% w/v) and magnesium chloride (5% w/v) was warn on the flaccid penis for 30-60 minutes before erection was desired. At that time, when sexual performance was needed, an erection was easily obtained and normal sexual activity was conducted.

Accordingly, it can be seen that in the present invention I have provided agents, which when applied to scalp lacking sufficient hair causes hair growth through utilization of one of the body's own mechanisms. This effect is achieved by providing the biochemical substrate at the local site from which nitric oxide is produced. Nitric oxide causes increased local blood flow, which enables the growth of hair. Further I have provided agents which when applied to leg ulcers cause healing through use of the body's own mechanisms. Still further I have provided agents that when applied to a penis subject to erectile dysfunction causes restoration of normal sexual function. This effect is achieved by providing the biochemical substrate at the local site from which the controlling substance, nitric oxide is produced. Nitric oxide causes increases in local blood flow allowing the body's own healing cells and substances to reach the ulcer site.

The treatments for hair loss, impotence and wound and ulcer healing discussed above can be performed with L-arginine or its derivatives without penetrants in a preferred concentration of 5% to 35%, with preferred concentrations greater than 10% with effectiveness greatest at concentration levels above 20%.

An effective concentration of L-arginine to produce the beneficial effects discussed herein can be reduced when a hostile biophysical environment is created which causes the L-arginine to cross the barrier of the skin. The skin barrier is harder to cross than the mucus membranes associated with the anus or inside the mouth or through the lower intestine when taken orally. Therefore to create an effective concentration of L-arginine a sufficient biophysical environment must be created corresponding to the concentration of L-arginine. With concentration of L-arginine or its derivatives below 5% to 0.25% it is desired to have a concentration of 10% to 90%, preferably from 25% to 75% of an ion donor such as a to create a high ionic strength environment.

With a concentration of 5% to 15% of L-arginine or its derivatives it is desired to have a concentration of 5% to 80%, preferably from 15% to 50% of an ion donor such as a to create a high ionic strength environment.

With a concentration of 15% to 25% of L-arginine or its derivatives it is desired to have a concentration of 5% to 50%, preferably from 10% to 30% of an ion donor such as a to create a high ionic strength environment.

A method of promoting hair growth, treating impotence or healing wounds comprising delivering a nitric oxide releasing substance selected from a member of the group consisting of L-arginine, L-arginine salts and L-arginine derivatives, to a selected area of the skin where hair growth is desired by topically applying to the selected area of skin where hair growth is desired a delivery vehicle for the substance, said delivery vehicle containing an effective amount of the substance, and a concentration of ionic salt sufficient to create a hostile biophysical environment which causes the substance to migrate from the delivery vehicle to the skin where the substance is absorbed by tissue wherein said delivery vehicle comprises water (20-80%), mineral oil (3-18%), glyceryl stearate (0.5-12%), squalene (0.2-12%), cetyl alcohol (0.1-11%), propylene glycol stearate (0.1-11%), wheat germ oil (0.1-6%), glyceryl stearate (0.1-6%), isopropyl myristate (0.1-6%), stearyl stearate (0.1-6%), polysorbate 60 (0.1-5%), propylene glycol (0.05-5%), tocopherol acetate (0.5-5%), collagen (0.05-5%), sorbitan stearate (0.05-5%), vitamin A&D (0.02%-4%), triethanolamine (0.01-4%), methylparaben (0.01-4%), aloe vera extract (0.01-4%), imidazolidinyl urea (0.01-4%), propylparaben (0.01-4%), bha (0.01-4%), L-arginine hydrochloride (5% to 25%), sodium chloride (5% to 25%), and magnesium chloride (5% to 25%) is applied to the selected area of skin where hair growth is desired.

I claim:

1. A method of increasing localized blood flow in tissues comprising the steps of:
    applying topically to the skin a delivery vehicle comprising L-arginine hydrochloride at a concentration of 0.25% to 25% by weight,
    wherein the L-arginine hydrochloride is contained in a package selected from the group consisting of liposomes, emulsions of collagen, collagen peptides and combinations thereof,
    wherein the delivery vehicle further comprises an ion donor selected from the group consisting of sodium chloride, choline chloride, potassium chloride, lithium chloride and magnesium chloride and mixtures thereof, and said ion donor is present in an amount sufficient to create a high ionic strength environment able to cause the L-arginine hydrochloride to migrate from the delivery vehicle to the skin where the delivery vehicle is applied,
    wherein (i) said ion donor concentration in the delivery vehicle is 10% to 90% by weight when the concentration of L-arginine hydrochloride in the delivery vehicle is 0.25% to below 5% by weight, (ii) said ion donor concentration in the delivery vehicle is 5% to 80% by weight when the concentration of L-arginine hydrochloride in the delivery vehicle is 5% to 15% by weight, and (iii) said ion donor concentration in the delivery vehicle is 5% to 50% by weight when the concentration of L-arginine hydrochloride in the delivery vehicle is greater than 15% to 25% by weight.

2. A topical delivery vehicle for application to the skin comprising:
    L-arginine hydrochloride at a concentration of 0.25% to 25% by weight,
    wherein the L-arginine hydrochloride is contained in a package selected from the group consisting of liposomes, emulsions of collagen, collagen peptides and combinations thereof,
    wherein the delivery vehicle further comprises an ion donor selected from the group consisting of sodium chloride, choline chloride, potassium chloride, lithium chloride and magnesium chloride and mixtures thereof, and said ion donor is present in an amount sufficient to create a high ionic strength environment able to cause the L-arginine hydrochloride to migrate from the delivery vehicle to the skin where the delivery vehicle is applied,
    wherein (i) said ion donor concentration in the delivery vehicle is 10% to 90% by weight when the concentration of L-arginine hydrochloride in the delivery vehicle is 0.25% to below 5% by weight, (ii) said ion donor concentration in the delivery vehicle is 5% to 80% by weight when the concentration of L-arginine hydrochloride in the delivery vehicle is 5% to 15% by weight, and (iii) said ion donor concentration in the delivery vehicle is 5% to 50% by weight when the concentration of L-arginine hydrochloride in the delivery vehicle is greater than 15% to 25% by weight.

3. A method of treating erectile dysfunction in a male comprising topically applying to the penis of a male with erectile dysfunction a delivery vehicle comprising L-arginine hydrochloride at a concentration of 0.25% to 25% by weight, wherein the L-arginine hydrochloride is contained in a package selected from the group consisting of liposomes, emulsions of collagen, collagen peptides and combinations thereof, wherein the delivery vehicle further comprises an ion donor selected from the group consisting of sodium chloride, choline chloride, potassium chloride, lithium chloride and magnesium chloride and mixtures thereof, and said ion donor is present in an amount sufficient to create a high ionic strength environment able to cause the L-arginine hydrochloride to migrate from the delivery vehicle to the skin where the delivery vehicle is applied, wherein (i) said ion donor concentration in the delivery vehicle is 10% to 90% by weight when the concentration of L-arginine hydrochloride in the delivery vehicle is 0.25% to below 5% by weight, (ii) said ion donor concentration in the delivery vehicle is 5% to 80% by weight when the concentration of L-arginine hydrochloride in the delivery vehicle is 5% to 15% by weight, and (iii) said ion donor concentration in the delivery vehicle is 5% to 50% by weight when the concentration of L-arginine hydrochloride in the delivery vehicle is greater than 15% to 25% by weight.

4. A method of promoting hair growth comprising:

Delivering L-arginine hydrochloride to a selected area of the skin where hair growth is desired by topically applying to the selected area of skin where hair growth is desired a delivery vehicle comprising the L-arginine hydrochloride at a concentration of 0.25% to 25% by weight, wherein the L-arginine hydrochloride is contained in a package selected from the group consisting of liposomes, emulsions of collagen, collagen peptides and combinations thereof, wherein the delivery vehicle further comprises an ion donor selected from the group consisting of sodium chloride, choline chloride, potassium chloride, lithium chloride and magnesium chloride and mixtures thereof, and said ion donor is present in an amount sufficient to create a high ionic strength environment able to cause the L-arginine hydrochloride to migrate from the delivery vehicle to the skin where the delivery vehicle is applied, wherein (i) said ion donor concentration in the delivery vehicle is 10% to 90% by weight when the concentration of L-arginine hydrochloride in the delivery vehicle is 0.25% to below 5% by weight, (ii) said ion donor concentration in the delivery vehicle is 5% to 80% by weight when the concentration of L-arginine hydrochloride in the delivery vehicle is 5% to 15% by weight, and (iii) said ion donor concentration in the delivery vehicle is 5% to 50% by weight when the concentration of L-arginine hydrochloride in the delivery vehicle is greater than 15% to 25% by weight.

* * * * *

UNITED STATES PATENT AND TRADEMARK OFFICE
CERTIFICATE OF CORRECTION

| | | |
|---|---|---|
| PATENT NO. | : 7,629,384 B2 | Page 1 of 1 |
| APPLICATION NO. | : 10/201635 | |
| DATED | : December 8, 2009 | |
| INVENTOR(S) | : Eric T. Fossel | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 833 days.

Signed and Sealed this

Second Day of November, 2010

David J. Kappos
*Director of the United States Patent and Trademark Office*